United States Patent
Brodkin et al.

(10) Patent No.: US 6,554,615 B1
(45) Date of Patent: Apr. 29, 2003

(54) PORCELAIN COMPOSITIONS FOR LOW EXPANSION ALL-PORCELAIN CORES AND ALLOYS

(75) Inventors: Dmitri Brodkin, West Orange, NJ (US); Carlino Panzera, Belle Mead, NJ (US); Paul Panzera, Mt. Holly, NJ (US)

(73) Assignee: Pentron Laboratory Technologies, LLC, Wallingford, CT (US)

( * ) Notice: Subject to any disclaimer, the term of this patent is extended or adjusted under 35 U.S.C. 154(b) by 379 days.

(21) Appl. No.: 09/887,668

(22) Filed: Jun. 30, 2000

Related U.S. Application Data

(60) Provisional application No. 60/142,203, filed on Jul. 2, 1999.

(51) Int. Cl.⁷ .................................................. A61C 5/08
(52) U.S. Cl. ................................ 433/222.1; 433/212.1; 106/35
(58) Field of Search ............................... 433/222.1, 218, 433/212.1, 202.1; 106/35

(56) References Cited

U.S. PATENT DOCUMENTS

| | | | | |
|---|---|---|---|---|
| 4,604,366 A | * | 8/1986 | Kacicz et al. .................. 501/6 |
| 5,009,709 A | * | 4/1991 | Ibsen et al. .................... 106/35 |
| 5,288,232 A | * | 2/1994 | Panzera et al. ............... 433/206 |
| 5,308,391 A | * | 5/1994 | Komma et al. ................ 106/35 |
| 5,314,334 A | * | 5/1994 | Panzera et al. ............... 433/206 |
| 5,329,695 A | * | 7/1994 | Traskos et al. ................ 29/830 |
| 5,374,453 A | * | 12/1994 | Swei et al. .................... 427/226 |
| 5,459,634 A | * | 10/1995 | Nelson et al. .............. 361/306.3 |
| 5,552,350 A | * | 9/1996 | Hornor ........................ 106/35 |
| 5,614,330 A | * | 3/1997 | Panzera et al. ................ 428/697 |
| 5,653,791 A | * | 8/1997 | Panzera et al. ................. 106/35 |

FOREIGN PATENT DOCUMENTS

| | | | |
|---|---|---|---|
| CA | 2239861 | * | 6/1998 |
| EP | 0 759 289 A2 | * | 2/1997 |
| WO | WO 96/18373 | * | 6/1996 |
| WO | WO 97/30678 | * | 8/1997 |
| WO | WO 99/18910 | * | 4/1999 |

* cited by examiner

*Primary Examiner*—Kevin Shaver
*Assistant Examiner*—Melba Bumgarner
(74) *Attorney, Agent, or Firm*—Ann M. Knab

(57) ABSTRACT

A dental porcelain composition comprises an amorphous glass phase with a maturing temperature less than about 850° C., wherein the amorphous glass phase, in one embodiment, comprises:

| Component | Amount (wt. %) |
|---|---|
| $SiO_2$ | 55–75 |
| $B_2O_3$ | 2.6–6 |
| $Al_2O_3$ | 3–4.9 |
| ZnO | 0–3 |
| CaO | 0–3 |
| MgO | 0.5–3 |
| $ZrO_2$ | 0–3 |
| BaO | 0–2 |
| $Li_2O$ | 0.8–2 |
| $K_2O$ | 0–6.5 |
| $Na_2O$ | 2–15 |
| $Tb_4O_7$ | 0–1 |
| $TiO_2$ | 0–3 |
| $CeO_2$ | 0–1 |
| F | 0–2 |

20 Claims, No Drawings

PORCELAIN COMPOSITIONS FOR LOW EXPANSION ALL-PORCELAIN CORES AND ALLOYS

This application claims the benefit of Provisional Application No. 60/142,203, filed Jul. 2, 1999.

BACKGROUND OF THE INVENTION

1. Field of the Invention

This invention relates to low expansion porcelain compositions, and in particular to relates to low expansion, low maturing temperature porcelain compositions useful for the fabrication of dental restorations.

2. Description of the Related Art

Porcelain materials are used in dentistry in order to obtain natural-looking dental restorations. Porcelains are highly desirable for this purpose since they can be colored to closely resemble the teeth they must replace, resist degradation inside the oral cavity, and remain biocompatible even after years of continuous contact with mammalian tissue. Restorations may be classified as either porcelain-fused-to-metal (PFM) or as all-ceramic restorations.

Typically, PFM restorations are fabricated by applying a dental porcelain powder in aqueous slurry to a metal alloy framework and firing the porcelain at high temperature to form a tight, impervious porcelain layer having the appearance of natural dentition. Those skilled in the art recognize that it is important that the firing temperature of the porcelain must be compatible with the material used for the metal framework. For example, titanium and titanium alloys require overlay porcelain having firing temperatures below the temperature at which the alpha crystalline structure transforms to the less useful beta crystalline structure. It is further important that the thermal expansion behavior of the porcelain be compatible with the thermal expansion behavior of the metal so that no stress cracks are produced in the porcelain layer due to thermal expansion mismatch stress occurring during firing and cooling down.

Today, there is an increasing trend in dentistry toward the use of ceramic cores in lieu of metal alloy frameworks to provide all-ceramic dental restorations. Where a ceramic is employed as the core of a dental restoration, any porcelain applied to the ceramic framework or coping must also possess a coefficient of thermal expansion (CTE) that is compatible with that of the ceramic in order to avoid production of stress cracks in the core and/or porcelain.

Metal alloys and ceramics employed in the manufacture of dental restorations have typically possessed moderately high coefficients of thermal expansion, in the range from about $13 \times 10^{-6}/°C$ to about $17 \times 10^{-6}/°C$. Many porcelain compositions are known in the art which are thermally compatible with these moderately high expansion core materials and provide smooth, fused glassy surface on the resulting dental restorations. However, few porcelain compositions are suitable for use with low expansion alloys and ceramics, i.e., those alloys and ceramics having coefficients of thermal expansion in the range of about $7 \times 10^{-6}/°C$ to about $13 \times 10^{-6}/°C$.

Accordingly, there remains a need in the art for porcelain compositions thermally compatible with low expansion core materials; having maturing temperatures below about 850° C.; which are chemically and thermally stable; and which provide a smooth, non-abrasive surface when applied to low expansion alloys and porcelains.

BRIEF SUMMARY OF THE INVENTION

The above mentioned drawbacks and disadvantages are overcome or alleviated by a dental porcelain composition comprising an amorphous glass phase with a maturing temperature less than about 850° C., wherein the amorphous glass phase, in one embodiment, comprises:

| Component | Amount (wt. %) |
| --- | --- |
| $SiO_2$ | 55–75 |
| $B_2O_3$ | 2.6–6 |
| $Al_2O_3$ | 3–4.9 |
| ZnO | 0–3 |
| CaO | 0–3 |
| MgO | 0.5–3 |
| $ZrO_2$ | 0–3 |
| BaO | 0–2 |
| $Li_2O$ | 0.8–2 |
| $K_2O$ | 0–6.5 |
| $Na_2O$ | 2–15 |
| $Tb_4O_7$ | 0–1 |
| $TiO_2$ | 0–3 |
| $CeO_2$ | 0–1 |
| F | 0–2 |

The above discussed and other features and advantages of the present invention will be appreciated and understood by those skilled in the art from the following detailed description.

DETAILED DESCRIPTION OF THE PREFERRED EMBODIMENTS

A dental porcelain composition which is low fusing and suitable for use with titanium, titanium alloys and ceramic cores, and which provides an extremely smooth surface for dental restorations, comprises an amorphous glass phase with a maturing temperature less than about 850° C. and a coefficient of thermal expansion (25° C. to 500° C.) of about $7 \times 10^{-6}/°C$ to about $11 \times 10^{-6}/°C$. The compositions find particular utility as overlay porcelains for veneers, single and multi unit restorations such as dental crowns and bridges (fixed partial dentures), inlays and onlays.

The dental porcelain composition comprises, on a weight percent basis:

| Oxide | Range 1 | Range 2 | Range 3 | Range 4 |
| --- | --- | --- | --- | --- |
| $SiO_2$ | 55–75 | 55–75 | 55–75 | 55–75 |
| $B_2O_3$ | 2.6–6 | 2.6–6 | 2.6–6 | 2.6–6 |
| $Al_2O_3$ | 3–4.9 | 3–9 | 3–9 | 2–4.9 |
| ZnO | 0–3 | 0–3 | 0–3 | 0–3 |
| CaO | 0–3 | 0–3 | 0–3 | 0–3 |
| MgO | 0.5–3 | 0–3 | 0–3 | 0.8–3 |
| $ZrO_2$ | 0–3 | 0–3 | 0–3 | 0–3 |
| BaO | 0–2 | 0–2 | 0–2 | 0–2 |
| $Li_2O$ | 0–8.2 | 0–2 | 0–2 | 0.8–2 |
| $K_2O$ | 0–6.5 | 0.5–4 | 0–6.5 | 6–10 |
| $Na_2O$ | 2–15 | 2–15 | 14.1–17 | 6–10 |
| $Tb_4O_7$ | 0–1 | 0–1 | 0–1 | 0–1 |
| $TiO_2$ | 0–3 | 0–3 | 0–3 | 0–3 |
| $CeO_2$ | 0–1 | 0–1 | 0–1 | 0–1 |
| F | 0–2 | 0–2 | 0–2 | 0–2 |
| Glass Transition Temperature, ° C. | 450–600 | 450–600 | 450–600 | 450–600 |
| Dilatometric Softening Temperature, ° C. | 520–650 | 520–650 | 520–650 | 520–650 |
| Firing Temperature, ° C. | Less than 850° C. | Less than 850° C. | Less than 850° C. | Less than 850° C. |
| CTE × $10^{-6}/°C$ (25° C.–500° C.) | 7–11 | 7–11 | 7–11 | 7–11 |

The dental porcelain compositions are amorphous glasses that mature at a temperature consistent with the thermal stability temperature of low expansion porcelain cores and alloy frameworks. That is, the porcelain forms a chemical bond with the core and has a thermal expansion value within about $2 \times 10^{-6}/°$ C. of that of the core. Components such as $Li_2O$, $BaO$, $F$, $TiO_2$, $ZnO$ and $SnO_2$ are added to these glasses to provide wettability and good bonding to the cores used with these porcelains. $ZnO$ and $TiO_2$ are particularly useful if the porcelain composition is to be used in conjunction with titanium and titanium alloys.

The porcelain compositions are chemically and thermally stable and have sufficient viscosity at firing temperature to maintain the required shape of dental restorations mimicking that of tooth anatomy. The porcelain compositions are fired at temperatures not exceeding about 850° C. The porcelain composition fires to nearly 100% of theoretical density, thus forming a tight impervious surface necessary in the oral environment.

A preferred feature of the present composition is a combination of $Al_2O_3$, $B_2O_3$, and $MgO$ effective to achieve low maturing temperature, while at the same time maintaining low thermal expansion and high chemical durability. While $B_2O_3$ often lowers thermal expansion and maturing temperature, it can simultaneously decrease the chemical durability of porcelain if it comprises more than about 3–4 wt % of the total composition. To lower expansion and maturing temperature while maintaining high chemical durability, $B_2O_3$ is therefore preferably used in combination with $Al_2O_3$ and $MgO$.

The porcelain compositions can be prepared by melting together sufficient precursor components to yield the compositions shown in the above table. Suitable precursors include silica, alumina, boric acid, feldspar, calcium carbonate, sodium carbonate, potassium carbonate, lithium carbonate or lithium fluoride, or if desired, the actual oxides, blended in proportion to yield the compositions shown in the above table.

The preparation of such materials is well known in the art. After the materials are blended, preferably in finely divided powder form such as powder sufficiently fine to pass through a 200 mesh screen (Tyler series), the precursors and/or oxides are heated to a temperature of at least about 1100° C., and preferably to at least about 1230° C., in a crucible to form a glass.

The molten glass may then be quenched in water, dried, and ground in a ball mill, to provide the porcelain material in the form of a powder.

It is preferred that the powder is ground finely enough so that it will pass through a 200 mesh screen (Tyler series). Opacifiers, pigments and fluorescing agents are then added to this powder in the amount of up to about 5 wt % for body and incisal porcelain compositions and up to 30 wt % for opaques.

The properties of the porcelain composition can be adjusted by applying the following well-known principles. Within the ranges of component proportions set forth in the above table, the coefficient of thermal expansion can be increased, if desired, by decreasing the proportion of $SiO_2$ and/or $B_2O_3$ and/or by increasing the proportion of the alkali metal oxides. The fusion point can be reduced by increasing the proportion of $B_2O_3$, $CaO$, and/or the alkali metal oxides. As between the two alkali metal oxides, an increase in the $Na_2O:K_2O$ ratio may lower the fusion point. However, when complex mixtures of alkali oxides are used, the so-called mixed alkali phenomenon affects the properties of the composition in a non-linear fashion. It is well within the skill of the porcelains art to apply these principles to make fine adjustments to the thermal expansion coefficients and fusion temperatures.

If desired, in order to achieve proper aesthetics, one or more layers of the porcelain composition can be applied over the core with each layer being separately fired. Thus, for example, an opaceous layer containing an opacifying agent such as $TiO_2$, $SnO_2$, $Al_2O_3$, $ZnO$, $CeO_2$, $ZrO$, $ZrSiO_4$ and the like can be applied over the core and fired. Thereafter, or in lieu thereof, a stain layer can be applied containing one or more conventional pigments such as vanadates, manganates, chromates, or other transition metal compounds, to tint the stain layer to the desired shade. The opaceous and/or stain layer can then be overcoated (after sequential firing) with a translucent layer of the porcelain composition of the present invention. In this manner, special effects can be obtained, e.g., a different shade at the tip of the restoration than at the gingival area. The layers are applied to the core in the usual manner, as by applying a paste of the porcelain powder in water over the core, shaping to the desired configuration, and then firing.

In an alternative embodiment, amorphous glasses in the form of powder (a frit) are mixed with a second glass flit, glass-ceramic frit and/or crystalline filler to modify the firing temperature and thermal expansion. Suitable crystalline fillers can be mullite or alumina particles to lower the thermal expansion to about 6 to about $7 \times 10^{-6}/°$ C. Preferably the average particle size of the crystalline filler is less than about 10 microns, and more preferably, less than about 3 microns. The second frit can be a lower maturing temperature glass to lower the composition's maturing temperature and increase the expansion to about $11 \times 10^{-6}/°$ C.

Preferred core materials include ceramics comprising lithium disilicate glass ceramics, zirconia, and micaceous glass ceramics, as well as other ceramic cores with thermal expansions in the range of about 7 to about $13 \times 10^{-6}/°$ C. Suitable metal and alloy cores include those based on Ti and Ti alloys.

The present method is further demonstrated by the following examples, which are meant to be illustrative, not limiting.

EXAMPLES

Table 1 shows exemplary formulations for the manufacture of the present porcelains. (All amounts are in weight percent.)

| Oxide | 1 | 2 | 3 | 4 | 5 | 6 | 7 | 8 | 9 | 10 | 11 |
|---|---|---|---|---|---|---|---|---|---|---|---|
| $SiO_2$ | 66.91 | 67.94 | 65.90 | 65.80 | 67.46 | 65.56 | 64.81 | 62.09 | 68.0 | 67.4 | 65.7 |
| $B_2O_3$ | 3.31 | 3.36 | 3.26 | 3.21 | 3.29 | 3.24 | 5.49 | 5.42 | 3.3 | 3.1 | 3.1 |
| $Al_2O_3$ | 4.84 | 4.92 | 4.77 | 4.80 | 4.92 | 4.74 | 4.83 | 7.94 | 4.9 | 4.9 | 4.9 |
| ZnO | 2.58 | 2.62 | 2.54 | 2.50 | 2.56 | 2.52 | 2.57 | 2.53 | 2.6 | 2.2 | 2.3 |
| CaO | 1.78 | 1.80 | 1.75 | 1.77 | 1.82 | 1.74 | 1.77 | 1.75 | 1.8 | 1.9 | 1.8 |

-continued

| Oxide | 1 | 2 | 3 | 4 | 5 | 6 | 7 | 8 | 9 | 10 | 11 |
|---|---|---|---|---|---|---|---|---|---|---|---|
| MgO | 1.28 | 1.30 | 1.26 | 1.22 | 1.25 | 1.25 | 1.27 | 1.26 | 1.3 | 1.2 | 1.2 |
| $ZrO_2$ | — | — | — | — | — | — | — | — | — | 0.1 | — |
| BaO | 1.21 | 1.23 | 1.20 | 1.18 | 1.21 | 1.19 | 1.21 | 1.19 | 1.2 | 1.0 | 1.1 |
| $Li_2O$ | 0.00 | 1.44 | 0.93 | 0.92 | 0.94 | 1.85 | — | 0.00 | 1.0 | 1.0 | 1.0 |
| $K_2O$ | 0.00 | 0.00 | 7.34 | 7.35 | 7.53 | 11.69 | — | 0.00 | 7.6 | 8.1 | 7.7 |
| $Na_2O$ | 14.71 | 11.95 | 7.73 | 8.02 | 8.22 | 2.88 | 14.67 | 14.48 | 8.3 | 8.7 | 8.10 |
| $Tb_4O_7$ | 0.59 | 0.60 | 0.58 | — | — | 0.58 | 0.59 | 0.58 | — | — | 0.52 |
| $TiO_2$ | 2.53 | 2.57 | 2.49 | 2.45 | 0.00 | 2.48 | 2.52 | 2.49 | — | — | 2.2 |
| $CeO_2$ | 0.27 | 0.28 | 0.27 | 0.79 | 0.81 | 0.27 | 0.27 | 0.27 | — | — | 0.24 |
| F | — | — | — | — | — | — | — | — | — | 0.3 | 0.2 |
| Glass Transition Temperature, ° C. | 545 | 520 | 526 | — | — | 523 | 574 | 574 | 520 | 510 | 510 |
| Dilatometric Softening Temperature, ° C. | 606 | 585 | 595 | — | — | 592 | 618 | 628 | — | — | — |
| Firing Temperature, ° C. | — | — | 800 | — | — | — | — | — | 800 | 760–770 | 760–770 |
| CTE × $10^{-6}$/° C. (25–500° C.) | 8.4 | 8.4 | 9.0 | — | — | 9.0 | 8.8 | 8.7 | 9.5 | 9.5–10 | 9.5 |

The porcelain composition of Example 3 was applied as an overlay porcelain on a heat-pressed lithium disilicate core (OPC 3G, available from American Thermocraft Corporation) and a micaceous core (Macor, available from Coming) which had been milled using a CAD/CAM device in the shape of crowns and three unit bridges. Both ceramic cores had a thermal expansion of about $10 \times 10^{-6}$/° C. Crowns were made using standard powder build-up techniques and fired at 800° C. No cracks were observed after 6 successive firings.

The two frit porcelain compositions of Examples 10 and 11 were applied as overlay porcelain on a heat-pressed lithium disilicate core (OPC 3G, available from American Thermocraft Corporation) in the shape of crowns and three unit bridges. These restorations were subjected to up to six firings at the temperature shown in the table. No cracking or distortion was observed.

The porcelain composition of Examples 3, 9 and 10 were applied to yttria stabilized tetragonal zirconia polycrystal (TZP) coping. The coping was produced from proprietary material provided by Coors Ceramics of Golden, Colo. by the process disclosed in co-pending, co-assigned U.S. patent application Ser. No. 09/376,921 which is incorporated by reference herein. These restorations were subjected to up to six firings at the temperature shown in the table. No cracking or distortion was observed.

The porcelain composition of Example 9 was used to make specimens for chemical solubility and strength measurements according to ISO 6872 and ISO 9694 specifications. Disks for chemical solubility testing and bars for 3 point bend test were wet condensed in the die and fired according to the ISO 6872 specifications. Solubility was 20 micrograms/cm2 and 3 point bend strength was 105±23 Mpa.

While preferred embodiments have been shown and described, various modifications and substitutions may be made thereto without departing from the spirit and scope of the invention. Accordingly, it is to be understood that the present invention has been described by way of illustration and not limitations.

What is claimed is:

1. A dental porcelain composition comprising an amorphous glass phase with a maturing temperature less than about 850° C., said amorphous glass phase comprising:

| Component | Amount (wt. %) |
|---|---|
| $SiO_2$ | 55–75 |
| $B_2O_3$ | 2.6–6 |
| $Al_2O_3$ | 3–4.9 |
| $Na_2O$ | 2–15 |
| MgO | 0.5–3 |
| $Li_2O$ | 0.8–2. |

2. The dental porcelain composition of claim 1 further comprising:

| Component | Amount (wt. %) |
|---|---|
| ZnO | 0–3 |
| CaO | 0–3 |
| $ZrO_2$ | 0–3 |
| BaO | 0–2 |
| $K_2O$ | 0–6.5 |
| $Tb_4O_7$ | 0–1 |
| $TiO_2$ | 0–3 |
| $CeO_2$ | 0–1 |
| F | 0–2 |

3. The dental composition of claim 1 further comprising a crystalline filler.

4. The dental composition of claim 1 further comprising a glass powder with a lower maturing temperature than said amorphous glass.

5. A dental restoration comprising a core and the dental porcelain composition of claim 1.

6. The dental restoration of claim 5 wherein the core is selected form the group consisting of lithium disilicate glass ceramics, zirconia, micaceous glass ceramics, titanium, and titanium alloys.

7. The dental restoration of claim 6 wherein the core has a coefficient of thermal expansion of about 7 to about $13 \times 10^{-6}$/° C.

8. A dental porcelain composition comprising an amorphous glass phase with a maturing temperature less than about 850° C., said amorphous glass phase comprising:

| Component | Amount (wt. %) |
|---|---|
| $SiO_2$ | 55–75 |
| $B_2O_3$ | 2.6–6 |
| $Al_2O_3$ | 2–4.9 |
| $Na_2O$ | 6–10 |
| $K_2O$ | 6–10 |
| $Li_2O$ | 0.8–2 |
| MgO | 0.8–3 |

9. The dental porcelain composition of claim 8 further comprising:

| Component | Amount (wt. %) |
|---|---|
| ZnO | 0–3 |
| CaO | 0–3 |
| $ZrO_2$ | 0–3 |
| BaO | 0–2 |
| $Tb_4O_7$ | 0–1 |
| $TiO_2$ | 0–3 |
| $CeO_2$ | 0–1 |
| F | 0–2 |
| $P_2O_5$ | 0–2 |

10. The dental composition of claim 8 further comprising crystalline filler.

11. The dental composition of claim 8 further comprising a glass powder with a lower maturing temperature than said amorphous glass.

12. A dental restoration comprising a core and the dental porcelain composition of claim 8.

13. The dental restoration of claim 12 wherein the core is selected from the group consisting of lithium disilicate glass ceramic, zirconia, micaceous glass ceramics, titanium and titanium alloys.

14. The dental restoration of claim 12 wherein the core has a coefficient of thermal expansion of about 7 to about $13 \times 10^{-6}/°$ C.

15. A dental porcelain composition comprising an amorphous glass phase with a maturing temperature less than about 850° C., said amorphous glass phase comprising:

| Component | Amount (wt. %) |
|---|---|
| $SiO_2$ | 55–75 |
| $B_2O_3$ | 2.6–6 |
| $Al_2O_3$ | 3–9 |
| $Na_2O$ | 2–15 |
| $K_2O$ | 0.5–4 |
| ZnO | 0–3 |
| CaO | 0–3 |
| MgO | 0–3 |
| $ZrO_2$ | 0–3 |
| BaO | 0–2 |
| $Li_2O$ | 0–2 |
| $Tb_4O_7$ | 0–1 |
| $TiO_2$ | 0–3 |
| $CeO_2$ | 0–1 |
| F | 0–2 |

16. The dental composition of claim 15 further comprising crystalline filler.

17. The dental composition of claim 15 further comprising a glass powder with a lower maturing temperature than said amorphous glass.

18. A dental porcelain composition comprising an amorphous glass phase with a maturing temperature less than about 850° C., said amorphous glass phase comprising:

| Component | Amount (wt. %) |
|---|---|
| $SiO_2$ | 55–75 |
| $B_2O_3$ | 2.6–6 |
| $Al_2O_3$ | 3–9 |
| $Na_2O$ | 14.1–17 |
| ZnO | 0–3 |
| CaO | 0–3 |
| MgO | 0–3 |
| $ZrO_2$ | 0–3 |
| BaO | 0–2 |
| $Li_2O$ | 0–2 |
| $K_2O$ | 0–6.5 |
| $Tb_4O_7$ | 0–1 |
| $TiO_2$ | 0–3 |
| $CeO_2$ | 0–1 |
| F | 0–2 |

19. The dental composition of claim 18 further comprising crystalline filler.

20. The dental composition of claim 18 further comprising a glass powder with a lower maturing temperature than said amorphous glass.

* * * * *

UNITED STATES PATENT AND TRADEMARK OFFICE
CERTIFICATE OF CORRECTION

PATENT NO.    : 6,554,615 B1
DATED         : April 29, 2003
INVENTOR(S)   : Brodkin et al.

It is certified that error appears in the above-identified patent and that said Letters Patent is hereby corrected as shown below:

<u>Title page, Item [54] and Column 1, lines 1-3,</u>
Delete the title "PORCELAIN COMPOSITIONS FOR LOW EXPANSION ALL PORCELAIN CORES AND ALLOYS" and replace with
-- PORCELAIN COMPOSITIONS FOR LOW EXPANSION ALL-CERAMIC CORES AND ALLOY FRAMEWORKS --.

Signed and Sealed this

Seventh Day of October, 2003

JAMES E. ROGAN
*Director of the United States Patent and Trademark Office*